US007011969B2

(12) United States Patent
Yoneda et al.

(10) Patent No.: US 7,011,969 B2
(45) Date of Patent: Mar. 14, 2006

(54) PRODUCTION PROCESS OF SURFACTIN

(75) Inventors: Tadashi Yoneda, Chiba (JP); Yoshiaki Miyota, Kanagawa (JP); Kazuo Furuya, Chiba (JP); Toshi Tsuzuki, Chiba (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 10/381,698

(22) PCT Filed: Sep. 28, 2001

(86) PCT No.: PCT/JP01/08568

§ 371 (c)(1),
(2), (4) Date: Jun. 27, 2003

(87) PCT Pub. No.: WO02/26961

PCT Pub. Date: Apr. 4, 2002

(65) Prior Publication Data

US 2004/0043451 A1    Mar. 4, 2004

Related U.S. Application Data

(60) Provisional application No. 60/258,560, filed on Dec. 29, 2000.

(30) Foreign Application Priority Data

Sep. 29, 2000  (JP)  .............................. 2000-300300

(51) Int. Cl.
*C12N 1/20* (2006.01)
(52) U.S. Cl. .............................. 435/252.31; 435/320.1; 435/69.1; 530/300
(58) Field of Classification Search ............ 435/252.31, 435/320.1, 69.1; 530/300, 350
See application file for complete search history.

(56) References Cited

U.S. PATENT DOCUMENTS

| | | | |
|---|---|---|---|
| 3,687,926 A | | 8/1972 | Arima et al. |
| 5,037,758 A | | 8/1991 | Mulligan et al. |
| 5,227,294 A | | 7/1993 | Carrera et al. |
| 6,060,051 A | * | 5/2000 | Heins et al. ............ 424/93.462 |

FOREIGN PATENT DOCUMENTS

| | | |
|---|---|---|
| EP | 0 463 393 A | 1/1992 |
| JP | 6-121668 A | 5/1994 |
| WO | WO 98 22598 A | 5/1998 |
| WO | WO 98 50422 A | 11/1998 |
| WO | WO 99/62482 * | 12/1999 |
| WO | WO 99 62482 A | 12/1999 |

OTHER PUBLICATIONS

Nakano, M. and Zuber, P. Journal of Bacteriology vol. 171, No. 10: 5347-5353 Oct. (1989).*
Wei, YH, Wang, LF, and Chang, JS Biotechnol. Prog. 20: 979-983 (2004).*
Hiraoka et al. J. Ferment Bioeng. 74:323-326 (1992).*
Nakayama S et al.: "Isolation of New Variants of Surfactin by a Recombinant *Bacillus subtilis*." *Applied Microbiology and Biotechnology*, vol. 48, No. 1, 1997, pp. 80-82, XP001124318.
Nakamura Kazuhiro et al: "Effect of High Magnetic Field on the Growth of *Bacillus subtilis* Measured in a Newly Developed Superconducting Magnet Biosystem." *Bioelectrochemistry and Bioenergetics*, vol. 43, No. 1, 1997, pp. 123-128, XP002219814.
Mulligan C N et al: "Enhanced Biosurfactant Production by a Mutant *Bacillus-subtilis* Strain." *Applied Microbiology and Biotechnology*, vol. 31, No. 5-6, 1989, pp. 486-489, XP008010002.
Ohno Akihiro et al: "Production of a Lipopeptide Antibiotic, Surfactin, by Recombinant *Bacillus subtilis* in Sold State Fermentation." *Biotechnology and Bioengineering*, vol. 47, No. 2, 1995, pp. 209-214, XP001109124.
First Office Action in Chinese Patent Application No. 01816513.3 dated Jun. 30, 2004.
Sakaguchi et al (1987), Nucleic Acids Research, vol. 15, No. 17, p. 7202.

* cited by examiner

Primary Examiner—Karen Cochrane Carlson
Assistant Examiner—Anand Desai
(74) Attorney, Agent, or Firm—Sughrue Mion, PLLC

(57) ABSTRACT

A process for producing Surfactin, comprising culturing a microorganism of the genus *Bacillus* in a liquid culture medium containing flour of beans such as soybean or an extract thereof as a nitrogen source and accumulating Surfactin in the culture broth, and a microorganism of the genus *Bacillus* which have an activity to produce a crude Surfactin in a concentration of from 8 to 50 g/L on culturing for 20 to 90 hours.

23 Claims, No Drawings

SEQUENCE LISTING

<160> NUMBER OF SEQ ID NOS: 4

<210> SEQ ID NO 1
<211> LENGTH: 36
<212> TYPE: DNA
<213> ORGANISM: Artificial Sequence
<220> FEATURE:
<223> OTHER INFORMATION: PCR primer

<400> SEQUENCE: 1
gtggtcgatg aaagagagct ttatcaaaca ggccgg                36

<210> SEQ ID NO 2
<211> LENGTH: 36
<212> TYPE: DNA
<213> ORGANISM: Artificial Sequence
<220> FEATURE:
<223> OTHER INFORMATION: PCR primer

<400> SEQUENCE: 2
ccggcctgtt tgataaagct ctctttcatc gaccac                36

<210> SEQ ID NO 3
<211> LENGTH: 46
<212> TYPE: DNA
<213> ORGANISM: Artificial Sequence
<220> FEATURE:
<223> OTHER INFORMATION: PCR primer

<400> SEQUENCE: 3
cccggatccg gactagtcta gagctctacg cgatctccgg gcgggc     46

<210> SEQ ID NO 4
<211> LENGTH: 36
<212> TYPE: DNA
<213> ORGANISM: Artificial Sequence
<220> FEATURE:
<223> OTHER INFORMATION: PCR primer

<400> SEQUENCE: 4
cccggatcct taagcttgag tacgacggtt tttctg                36

PRODUCTION PROCESS OF SURFACTIN

CROSS REFERENCE TO THE RELATED APPLICATIONS

This application is a 35 U.S.C. 371 national stage filing of international application PCT/JP01/08568, filed Sep. 28, 2001, which claims benefit under 35 U.S.C 119 of U.S. application 60/258,560, filed Dec. 29, 2000.

TECHNICAL FIELD

The present invention relates to a process for producing Surfactin using a microorganism of the genus *Bacillus* in high productivity. More specifically, the present invention relates to a process for producing Surfactin comprising culturing a microorganism of the genus *Bacillus* in a liquid culture medium containing flour of beans such as soybean or an extract thereof as a nitrogen source and accumulating Surfactin in the culture broth, and to a microorganism of the genus *Bacillus* which is useful for the process.

BACKGROUND ART

It is conventionally known that microorganisms of the genus *Bacillus*, particularly *Bacillus subtilis*, produce Surfactin. The structure of Surfactin has been reported, for example, by Kakinuma et al. in *Agric. Biol. Chem.*, 33, 971–972 (1969), *Agric. Biol. Chem.*, 33, 973–976 (1969) and *Agric. Biol. Chem.*, 33, 1523–1524 (1969).

Surfactin has an activity of decreasing the surface tension at a low concentration of 10 ppm or less and is easily biodegradable, therefore, the Surfactin has been taken notice of as an excellent surfactant. With respect to the process for producing Surfactin, the following methods are known. For example, K. Arima et al. disclose a method of producing Surfactin using a *Bacillus subtilis* strain ATCC 21331 or ATCC 21332 (see, U.S. Pat. No. 3,687,926 and *Biochem. Bioph. Res. Commun.*, 31, 488–494 (1968)) and state that according to this method, from 0.05 to 0.1 g/L of Surfactin is accumulated in the culture medium by the culturing for 24 hours.

Since this productivity of Surfactin is low for the industrial use, a large number of inventors have made efforts to improve the productivity. Cooper et al. disclose a method of producing Surfactin while continuously removing foam generated during the culturing of *Bacillus subtilis* ATCC 21332 (see, *Appl. Environ. Microbiol.*, 42, 408–412 (1981)). According to this method, the yield of Surfactin is from 0.7 to 0.8 g/L.

Sheppard et al. disclose a method of growing *Bacillus subtilis* in a culture medium containing hydrolyzed peat and thereby achieving a yield of 0.16 g/L (see, *Appl. Microbiol. Biotechnol.*, 27, 110–116 (1987)). Mulligan et al. disclose a method for improving the yield of Surfactin by using a mutant strain of *Bacillus subtilis* ATCC 21332 (see, *Appl. Microbiol. Biotech.*, 31, 486–489 (1989)). According to this method, the yield of Surfactin after culturing for 40 hours is 0.562 g/L.

Okuda et al. disclose a method for increasing the yield of Surfactin by culturing *Bacillus subtilis* in a magnetic field (see, JP-A-6-121668 (the term "JP-A" as used herein means an "unexamined published Japanese patent application")). Wei et al. disclose a method for increasing the yield of Surfactin by culturing *Bacillus subtilis* ATCC 21332 while adding an iron in a high concentration (see, *Enz. Microbiol. Technol.*, 22, 724–728 (1998)), where the yield of Surfactin is 3.5 g/L.

Carrera et al. disclose that *Bacillus subtilis* ATCC 55033 as a mutant strain of *Bacillus subtilis* ATCC 21332 has an activity to produce Surfactin in a concentration of 2.0 to 4.0 g/L (see, Japanese Patent No. 3030789, U.S. Pat. No. 5,227,294). Kim et al. disclose that Surfactin is produced in a concentration of 7.0 g/L when *Bacillus subtilis* C9 is cultured under the conditions of oxygen limitation using glucose as a carbon source and $NH_4HCO_3$ as a nitrogen source (see, *J. Ferment. Bioeng.*, 84, 41–46 (1997)).

These improvements are, however, not sufficient for the industrial use of Surfactin. A strain having a higher productivity and a production process for further elevating the productivity are being demanded.

SUMMARY OF INVENTION

One of the objects of the present invention is to provide a microorganism of the genus *Bacillus*, which can produce Surfactin in a high yield. Another object of the present invention is to provide a process for producing Surfactin, where a Surfactin-producing microorganism of the genus *Bacillus* is cultured and the Surfactin is accumulated in a high concentration in the culture broth.

In order to overcome the above-described problems, the present inventors have made extensive investigations on various culture medium ingredients. As a result, it has been found that when a Surfactin-producing microorganism of the genus *Bacillus* is cultured in a culture medium containing flour of beans such as soybean or an extract thereof as a nitrogen source, Surfactin is accumulated in a high concentration in the culture broth, and that means for removing foam is not necessary because excess foam generation is prevented during the production of Surfactin by this method. Furthermore, it has also been found that when the Surfactin-producing microorganism of the genus *Bacillus* is modified and the modified microorganism is cultured in the culture medium, Surfactin is accumulated in a high concentration in the culture broth. The present invention has been accomplished based on these findings.

More specifically, the present invention relates to a process for producing Surfactin described in [1] to [20] below and a microorganism of the genus *Bacillus* described in [21] to [26] below.

[1] A process for producing Surfactin, comprising culturing a microorganism of the genus *Bacillus* in a liquid culture medium containing flour of beans or an extract thereof and accumulating Surfactin in the culture broth.

[2] The process for producing Surfactin as described in [1] above, wherein the beans is selected from the group consisting of soybean, adzuki bean, pea, broad bean, chick pea, lentil and string bean.

[3] The process for producing Surfactin as described in [2] above, wherein the beans is soybean.

[4] The process for producing Surfactin as described in any one of [1] to [3] above, wherein a microorganism of the genus *Bacillus* is cultured in a liquid culture medium containing a yeast extract.

[5] The process for producing Surfactin as described in any one of [1] to [4] above, comprising the steps of
culturing the microorganism of the genus *Bacillus* at a pH of 6 to 9 and a temperature of 25 to 42° C. for 20 to 90 hours under aerobic conditions in a liquid culture medium further containing a catabolizable carbon source, a catabolizable nitrogen source and an inorganic salt, accumulating Surfactin in the culture broth without removing the generated foam from the fermentation vessel, and separating and purifying Surfactin from the obtained culture broth.

[6] The process for producing Surfactin as described in any one of [1] to [5] above, wherein Surfactin is accumulated in the culture broth in a concentration of from 8 to 50 g/L.

[7] The process for producing Surfactin as described in any one of [1] to [6] above, wherein the microorganism of the genus *Bacillus* is *Bacillus subtilis*.

[8] The process for producing Surfactin as described in [7] above, wherein *Bacillus subtilis* is *Bacillus subtilis* SD901 (FERM BP-7666) or a mutant strain thereof.

[9] The process for producing Surfactin as described in any one of [1] to [8] above, wherein the concentration of flour of beans or an extract thereof in the culture broth is from 0.5 to 20 w/w %.

[10] The process for producing Surfactin as described in any one of [5] to [9] above, wherein the catabolizable carbon source is one or more members selected from the group consisting of glucose, maltose, sucrose, hydrolyzed starch, molasses, potato extract, malt, peat, vegetable oil, corn steep liquor, fructose, syrup, sugar, liquid sugar, invert sugar, alcohol, organic acid, organic acid salts and alkane.

[11] The process for producing Surfactin as described in [10] above, wherein the catabolizable carbon source is glucose or maltose.

[12] The process for producing Surfactin as described in any one of [5] to [11] above, wherein the catabolizable nitrogen source is an ammonium salt or an inorganic or organic nitrogen.

[13] The process for producing Surfactin as described in [12] above, wherein the ammonium salt is ammonium nitrate, ammonium sulfate, ammonium chloride, ammonium acetate, ammonium carbonate or ammonium bicarbonate.

[14] The process for producing Surfactin as described in [12] or [13] above, wherein the inorganic or organic nitrogen is one or more members selected from the group consisting of ammonia, sodium nitrate, potassium nitrate, sodium glutamate, urea, peptone, meat extract, corn steep liquor, casein hydrolysate, feather meal and yeast extract.

[15] The process for producing Surfactin as described in any one of [5] to [14] above, wherein the cation contained in the inorganic salt is potassium ion, sodium ion, magnesium ion, iron ion, manganese ion, calcium ion, zinc ion, cobalt ion, nickel ion, copper ion or molybdenum ion and the anion is phosphate ion, sulfate ion, chloride ion or nitrate ion.

[16] The process for producing Surfactin as described in any one of [1] to [15] above, wherein an amino acid and/or a vitamin is contained in the culture medium.

[17] The process for producing Surfactin as described in [16] above, wherein the amino acid is one or more members selected from the group consisting of L-glycine, L-aranine, L-valine, L-leucine, L-isoleucine, L-serine, L-threonine, L-phenylaranine, L-tyrosine, L-cysteine, cystine, L-metyonine, L-tryptophan, L-histidine, L-proline, L-asparaginic acid, L-asparagine, L-glutamic acid, L-glutamine, L-arginine, L-lycine, D-valine and D-isoleucine.

[18] The process for producing Surfactin as described in [16] or [17] above, wherein the vitamin is one or more members selected from the group consisting of biotin, thiamin, riboflavin, pyridoxine, nicotinic acid, nicotinic acid amide, pantothenic acid, pyridoxal, pyridoxine, myo-inositol, choline, folic acid, cobalamin and cyanocobalamin.

[19] The process for producing Surfactin as described in any one of [4] to [18] above, wherein the pH is from 6.9 to 7.5.

[20] The process for producing Surfactin as described in any one of [4] to [19] above, wherein the temperature is from 30 to 37° C.

[21] A microorganism of the genus *Bacillus*, which have an activity to produce a crude Surfactin in a concentration of from 8 to 50 g/L on culturing for 20 to 90 hours.

[22] The microorganism of the genus *Bacillus* as described in [21] above, which have an activity to produce Surfactin in a concentration of from 8 to 50 g/L on culturing for 20 to 90 hours in a liquid culture medium containing flour of beans or an extract thereof.

[23] The microorganism of the genus *Bacillus* as described in [22] above, wherein the beans is soybean.

[24] The microorganism of the genus *Bacillus* as described in any one of [21] to [23] above, which is *Bacillus subtilis*.

[25] The microorganism of the genus *Bacillus* as described in [24] above, wherein *Bacillus subtilis* is *Bacillus subtilis* SD901 (FERM BP-7666) or a mutant strain thereof.

[26] *Bacillus subtilis* SD901 (FERM BP-7666) or a mutant strain thereof.

DETAILED DESCRIPTION OF INVENTION

The present invention is described in detail below.

According to the present invention, a Surfactin-producing microorganism is cultured by adding flour of beans such as soybean or an extract thereof as a nitrogen source to the culture medium where the microorganism is cultured, whereby Surfactin can be accumulated in a high concentration in the culture broth.

According to the knowledge of the inventors, culturing of a microorganism of the genus *Bacillus* in a culture medium containing flour of beans or an extract thereof as a nitrogen source is conventionally known to one skilled in the art, however, the production process of culturing a Surfactin-producing microorganism in a culture medium containing flour of beans or an extract thereof as a nitrogen source and accumulating the Surfactin in a high concentration in the culture broth is not known and newly found by the present inventors.

The beans which can be used in the present invention include soybean, adzuki bean (red bean), pea, broad bean, chick pea, lentil and string bean. These may be used individually or in combination thereof. Among these, soybean is preferred.

The microorganism of the genus *Bacillus* for use in the present invention is not particularly limited insofar as it produces Surfactin, however, for example, *Bacillus subtilis* SD901 modified by the present inventors is suitable.

This strain is a novel mutant strain of *Bacillus subtilis* and is characterized by the activity of accumulating Surfactin in a high concentration. This strain is distinguished from conventional strains in the point of having an extremely high productivity of Surfactin and it is proper to designate the strain as a novel strain of *Bacillus subtilis*. This novel strain is named as *Bacillus subtilis* SD901 and deposited at Bioengineering Industrial Technology Laboratory, Institute of Industrial Science and Technology, Ministry of International Trade and Industry, Japan on Aug. 7, 2000 under accession number FERM P-17989 and transferred to international deposition under the international accession number FERM BP-7666 at International Patent Organism Depositary, National Institute of Advanced Industrial Science and Technology of AIST Tsukuba Central 6, 1–1, Higashi 1-chome, Tsukuba-shi, Ibaraki-ken 305–8566 Japan on Jul. 16, 2001.

Accordingly, the *Bacillus subtilis* SD901 (FERM BP-7666) itself is a subject of the present invention. Mutant strains derived from this strain and having the same properties as this strain in the point of having an extremely high productivity of Surfactin are included in the present invention.

Also, a microorganism of the genus *Bacillus* which have an activity to produce a crude Surfactin in a concentration of from 8 to 50 g/L on culturing for 20 to 90 hours is a subject of the present invention.

Describing more specifically the present invention, the *Bacillus subtilis* SD901 (FERM BP-7666) of the present invention is originated in *Bacillus subtilis* MI113 (pC115) that is a transformant of *Bacillus subtilis* MI113 as a mutant strain of *Bacillus subtilis* Marburg 168 strain.

The *Bacillus subtilis* MI113 (pC115) is described in the publication of Nakayama et al. (see, *Appl. Microbiol. Biotechnol.*, 48, 80–82 (1997)). The plasmid pC115 is described in the publication of Huang et al. (see, *J. Ferment. Bioeng.*, 76, 6, 445–450 (1993)). The gene lpa-14 on the plasmid pC115, which participates in the production of Surfactin, is connected with the plasmid pNS1981 originated in *Bacillus subtilis* to form a plasmid, thereby transforming the *Bacillus subtilis* MI113. The lpa-14 is described in the publication of Hiraoka et al. (see, *J. Ferment. Bioeng.*, 74, 5, 323–326 (1992)). The plasmid pNS1981 is described in the publication of Shishido et al. (see, *Plasmid*, 10, 224–234 (1983)).

The *Bacillus subtilis* SD901 (FERM BP-7666) of the present invention is acquired by the mutation of the transformant obtained above. For this purpose, a strain stock changed in the Surfactin yield is prepared by allowing a chemical or physical mutagen to act on the obtained transformant and from this, a colony increased in the productivity is isolated, thereby obtaining the *Bacillus subtilis* SD901 (FERM BP-7666).

Examples of the chemical mutagen which can be used include EMS (ethyl methane sulfonate), diethyl sulfate and NTG (N-methyl-N'-nitro-N-nitrosoguanidine). Examples of the physical mutagen which can be used include ultraviolet ray, gamma ray and X-ray each in an amount of inducing mutagenesis.

Examples of the method for preparing a mutant strain stock include a method where *Bacillus subtilis* grown until the logarithmic growth phase in a nutrient culture medium such as Nutrient Broth (produced by Difco Laboratories) are harvested, washed and then suspended in a physiological saline, a mutagenesis-inducing amount of NTG is added to the suspension broth to induce mutagenesis, and the cells are again harvested, washed to remove NTG and again cultured in a nutrient culture medium such as Nutrient Broth (produced by Difco Laboratories), thereby preparing a mutant strain stock.

For isolating the colony increased in the productivity, for example, the mutant strain stock is appropriately diluted and spread on a plate culture medium prepared by adding agar to a culture medium such as Tryptose Blood Agar Base (TBAB; produced by Difco Laboratories) having added thereto an ovine blood and a mutant strain capable of producing Surfactin in a high concentration can be selected by comparing the sizes of clear zones formed around the colonies of grown *Bacillus subtilis*.

In fact, Mulligan et al. have revealed that the size of the formed clear zone is in proportion to the amount of Surfactin produced by *Bacillus subtilis* (see, *J. Ferment. Technol.*, 62, 158–179 (1984)). Subsequently, the thus-isolated mutant strain of *Bacillus subtilis* is subjected to test tube culturing using MI113 (pC115) as a control, whereby the Surfactin productivity can be confirmed. By such a method, *Bacillus subtilis* SD901 (FERM BP-7666) of the present invention can be obtained.

The production process of Surfactin of the present invention is illustrated with the case of soybean which is preferred among the beans. For most simply and conveniently performing the production process of Surfactin, for example, *Bacillus subtilis* SD901 (FERM BP-7666) is cultured in a nutrient culture medium such as Luria Broth containing 10 ppm of tetracycline at a temperature of 25 to 42° C., preferably from 28 to 400C, more preferably from 30 to 37° C. for approximately from 5 to 24 hours, the obtained culture broth is inoculated in a concentration of 0.1 to 10 w/w %, preferably from 0.5 to 7 w/w%, more preferably from 1 to 5 w/w % in a culture medium containing soybean flour or an extract thereof as a nitrogen source, and the cells are cultured at a temperature of 25 to 42° C., preferably from 28 to 40° C., more preferably from 30 to 37° C. for approximately from 20 to 90 hours. If the temperature departs from the above-described range, the production of Surfactin disadvantageously decreases to an extreme extent.

Among the term "flour of beans or an extract thereof" as used in the present invention, soybean flour or an extract thereof means soybean coarse grain obtained from pulverizing soybean or nonfat soybean granularly, pulverized soybean flour or an extract thereof such as hot water extract, or hydrolysate such as acid hydrolysate and enzyme hydrolysate, or the like. The concentration of the soybean flour or an extract thereof is not particularly limited, however, since the production of Surfactin increases in proportion to the concentration of soybean flour or an extract thereof in the culture medium, the concentration is preferably 0.5 w/w % or more for obtaining a high production to some extent. However, if the concentration of soybean flour or an extract thereof is high, insufficient sterilization may result, therefore, it is preferred that the concentration of soybean flour or an extract thereof does not exceed 20 w/w %. Accordingly, for obtaining a high production, the concentration of soybean flour or an extract thereof is from 0.5 to 20 w/w %, preferably from 2 to 15 w/w %, more preferably from 4 to 12 w/w %.

In addition to the soybean flour or an extract thereof, the culture medium for use in the present invention may contain a catabolizable carbon source, a catabolizable nitrogen source and an inorganic salt, which are commonly used. If desired, an amino acid and/or a vitamin may also be further added.

Examples of the catabolizable carbon source which can be used include glucose, maltose, sucrose, hydrolyzed starch, molasses, potato extract, malt, peat, vegetable oil, corn steep liquor, fructose, syrup, sugar, liquid sugar, invert sugar, alcohol, organic acid, organic acid salts, alkane and other general carbon sources. These may be used individually or in combination thereof. Among these, glucose and maltose are preferred. The catabolizable carbon source can be used usually in a concentration of 0.01 to 50 w/w %, preferably on the order of 1 to 40 w/w %.

Examples of the catabolizable nitrogen source which can be used include ammonium salts such as ammonium nitrate, ammonium sulfate, ammonium chloride, ammonium acetate, ammonium carbonate and ammonium bicarbonate and those containing inorganic or organic nitrogen, such as ammonia, sodium nitrate, potassium nitrate, sodium glutamate, urea, peptone, meat extract, corn steep liquor, casein hydrolysate, feather meal and yeast extract. These may be used individually or in combination thereof. Among these, a yeast extract is preferred in view of the Surfactin productivity. The catabolizable nitrogen source is suitably used in a concentration of generally from 0.01 to 30 w/w %, preferably on the order of 0.1 to 10 w/w %.

Furthermore, a cation or an anion is preferably added as an inorganic salt and examples thereof include potassium ion, sodium ion, magnesium ion, iron ion, manganese ion, calcium ion, zinc ion, cobalt ion, nickel ion, copper ion, molybdenum ion, phosphate ion, sulfate ion, chloride ion and nitrate ion. The concentration added varies depending on the culturing conditions, however, it is usually from 0.01 to 5 w/w % for the phosphate, from 10 ppm to 2 w/w % for the magnesium salt and approximately from 0.1 ppm to 1,000 ppm for other salts.

Examples of the amino acid added include L-glycine, L-aranine, L-valine, L-leucine, L-isoleucine, L-serine, L-threonine, L-phenylaranine, L-tyrosine, L-cysteine, cystine, L-metyonine, L-tryptophan, L-histidine, L-proline, L-asparaginic acid, L-asparagine, L-glutamic acid, L-glutamine, L-arginine, L-lysine, D-valine and D-isoleucine and one or more thereof can be added. In the present invention, L-arginine and L-tryptophan are particularly preferred. The concentration added is from 0.001 to 5 w/w %, preferably on the order of 0.01 to 1 w/w %.

Examples of the vitamin include biotin, thiamin, riboflavin, pyridoxine, nicotinic acid, nicotinic acid amide, pantothenic acid, pyridoxal, pyridoxine, myo-inositol, choline, folic acid, cobalamin and cyanocobalamin and one or more thereof can be added. The concentration added is from 0.1 to 100 ppm, preferably from 1 to 50 ppm.

In the present invention, the culturing is performed by adding the above-described culture medium to a vessel such as test tube, flask or fermenter, under vigorous aeration. It is not particularly necessary to remove foam generated.

In conventional culturing methods, since foaming vigorously occurs accompanying the accumulation of Surfactin and the culturing becomes difficult, the foam are removed during culturing and Surfactin contained therein is recovered. However, such a method cannot be implemented in an industrial scale. It is considered that in the present invention, the foam generated during culturing need not be removed because the accumulated Surfactin adsorbs to insoluble matters originated in the soybean flour or an extract thereof in the culture medium and thereby excess foaming is suppressed and also because the ingredients originated in the soybean flour or an extract thereof have an effect of suppressing the foaming. By virtue of these, production in an industrial scale can be implemented similarly to ordinary production by fermentation. In the culture medium having added thereto soybean flour or an extract thereof, insoluble matters originated therein are present, so that the culture medium can be free of high osmotic pressure as compared with a culture medium having added thereto a soluble ingredient in the same concentration. The insoluble matters are gradually solubilized and consumed during culturing, so that production by fermentation can be implemented in a culture medium containing a nutrient source in a high concentration and Surfactin can be produced in a high yield.

In the case of using a vessel such as test tube or flask, the aeration is performed by strongly shaking the vessel and the initial pH of the culture medium is adjusted to 6.5 to 8.0.

In the case of performing the high-concentration production using a vessel such as fermenter, the culturing is performed with stirring while passing a sterilized air and when the culturing becomes difficult due to foaming, a commonly used antifoaming agent may be added.

The culture medium is preferably maintained at a pH of 6 to 9, preferably from 6.5 to 8.0, more preferably from 6.9 to 7.5. The pH is adjusted by adding an aqueous basic solution such as an aqueous solution of ammonia, potassium hydroxide, sodium hydroxide, sodium carbonate and potassium carbonate. Among these, sodium hydroxide and aqueous ammonia are preferably used. The concentration is preferably on the order of 20 w/w % for sodium hydroxide and from 8 to 25 w/w % for aqueous ammonia. By performing the culturing under such preferred conditions, a culture broth containing a crude Surfactin in a concentration of 8 to 50 g/L can be obtained within 20 to 90 hours.

From this culture broth, Surfactin can be recovered and purified. The purification can be performed by a known method such that the culture broth is rendered acidic by adding sulfuric acid, hydrochloric acid or nitric acid and the precipitated Surfactin is subjected to ultrafiltration, extraction with an organic solvent such as methanol or dichloromethane, treatment with an activated carbon or crystallization. In place of the precipitation by the addition of an acid, precipitation by the addition of a calcium salt may be used.

In this way, purified Surfactin can be obtained in an amount of from 6 to 40 g per 1 L of the culture medium.

The Surfactin obtained according to the present invention can be used, for example, in the field of detergent, emulsifier, wetting agent, dispersant, solubilizing agent, antistatic agent, anticlouding agent, lubricant, pipe resistance lowering agent and the like, and is effective for cosmetics, food, medical preparations, agricultural chemicals, ink and the like.

BEST MODE FOR CARRYING OUT THE INVENTION

The present invention is described in greater detail below by referring to Examples, however, the present invention is by no means limited to these Examples.

EXAMPLE 1

Preparation of *Bacillus subtilis* Transformant

*Bacillus subtilis* MI113 (pC115) was inoculated in 50 ml of Luria Broth (1 w/v % polypeptone, 0.5 w/v % yeast extract and 0.5 w/v % NaCl with the balance being water) having added thereto 5 ppm of chloramphenicol and cultured at 35° C. and 150 rpm for 16 hours. Thereafter, the cells were recovered by the centrifugation and therefrom, plasmid pC115 was recovered by an alkali method (see, *Molecular cloning a laboratory manual*, second edition, Cold Spring Harbor Laboratory Press). Using pC115 as a template and four kinds of synthetic DNA having a base sequence shown below as a primer, PCR was performed to acquire a lpa14 gene fragment having a BamHI cut site at the 5'-terminal and the 3'-terminal, where the internal Hindu cut site was deleted and the amino acid sequence did not change.

5'-GTGGTCGATGAAAGAGAGCTTTATCAAACAGGCCGG-3' (sequence ID No. 1)

5'-CCGGCCTGTTTGATAAAGCTCTCTTTCATCGACCAC-3' (sequence ID No. 2)

5'-CCCGGATCCGGACTAGTCTAGAGCTCTACGCGATCTCCGGGCGGGC-3' (sequence ID No. 3)

5'-CCCGGATCCTTAAGCTTGAGTACGACGGTTTTTCTG-3' (sequence ID No. 4)

The obtained lpa14 gene fragment and the plasmid pN1981 were each cut by BamHI (produced by Takara Shuzo Co., Ltd.) and ligated, whereby Bacillus subtilis MI113 was transformed according to a modified method of Anagnostopoulos and Spizizen (see, Biseibutsu Idengaku Jikkenho, Idengaku Jikkenho Koza 3 (Microorganism Genetics Experimental Method, Genetics Experimental Method Course 3), published by Kyoritsu Shuppan). Thus, a Bacillus subtilis transformant to be grown on Luria agar plate having added thereto 10 ppm of tetracycline (1 w/v % polypeptone, 0.5 w/v % yeast extract and 0.5 w/v % NaCl, 2 w/v % agar with the balance being water) was obtained.

EXAMPLE 2

Preparation of Bacillus subtilis SD901 (FERM BP-7666)

The Bacillus subtilis transformant was inoculated in 5 ml of an L culture medium having added thereto 10 ppm of tetracycline and cultured at 35° C. and 300 rpm for 16 hours. Subsequently, the obtained culture broth was inoculated in a concentration of 1 v/v % in 5 mL of the same culture medium and cultured at 35° C. and 300 rpm until the OD660 became 0.2. Thereafter, the cells were recovered by centrifugation and after discarding the supernatant, washed three times with 5 ml of a phosphate buffer saline (0.8% NaCl, 0.02% KCl, 0.144% $Na_2HPO_4$ and 0.024% $KH_2PO_4$, the pH was adjusted to 7.4 by HCl) and again suspended in 0.5 ml of the same buffer solution.

To the suspension, 0.05 ml of an aqueous 2000 ppm N-methyl-N'-nitro-N-nitrosoguanidine solution was added and left standing at 30° C. for 10 minutes. The suspension was centrifuged, the supernatant was discarded and the cells was washed three times with 5 ml of the same buffer solution and again suspended in 1 ml of a new L culture medium. The suspension was added to 4 ml of an L culture medium having added thereto 10 ppm of tetracycline, the cells were grown at 35° C. overnight, 2.5 ml of an aqueous 50 w/w % glycerol solution was added, the resulting culture broth was dispensed aliquots of the broth into several vials for cyropreservation and stored at −135° C. to prepare a transformant storage stock.

Subsequently, the transformant storage stock diluted with a sterilized water was spread on an agar plate culture medium (see, Cooper et al, Appl. Environ. Microbiol., 42, 408–412 (1981)) containing 5 w/v % ovine blood, 4 w/v % glucose, 0.1 w/v % Nutrient Broth (produced by Difco Laboratories) and 0.1% yeast extract to form about 200 colonies/plate. After the incubation at 35° C for 20 to 48 hours, clear zones formed around the grown colonies were observed and the colonies having formed in the periphery thereof a large clear zone were selected as a Surfactin high production strain. One of these strains is named as Bacillus subtilis SD901 and deposited under the accession number FERM BP-7666.

EXAMPLE 3

Effect of Nitrogen Source on Production of Surfactin in Test Tube Culturing

Bacillus subtilis SD901 (FERM BP-7666) was streaked on an L plate culture medium having added thereto 10 ppm of tetracycline and grown at 35° C. overnight. Thereafter, 1 ml of a culture medium having the following composition A was dispensed into a test tube and in this culture medium, one loop of cells picked up from the L plate culture medium were inoculated and cultured at 35° C. for 72 hours.

| Composition A (w/w %) | |
|---|---|
| 1.4% | $K_2HPO_4$ |
| 0.6% | $KH_2PO_4$ |
| 0.1% | sodium citrate |
| 0.02% | $MgSO_4.7H_2O$ |
| 0.005% | $FeSO_4.7H_2O$ |
| 3 ppm | $MnCl_2.4H_2O$ |
| 1 ppm | $ZnCl_2$ |
| 0.1 ppm | $CoCl_2.6H_2O$ |
| 0.02 ppm | $CuCl_2.2H_2O$ |
| 0.02 ppm | $Na_2MoO_4.2H_2O$ |
| 3% | glucose |
| 0.01% | yeast extract |
| 0.1% | L-tryptophan |
| 0.1% | L-arginine |

To the above-described composition, one of the following nitrogen sources was added.

| | |
|---|---|
| 0.5 w/w % | soybean flour |
| 0.5 w/w % | potassium nitrate |
| 0.5 w/w % | ammonium nitrate |
| 0.5 w/w % | ammonium sulfate |
| 0.5 w/w % | urea |
| 0.5 w/w % | sodium glutamate |
| 0.5 w/w % | peptone |

The culture broth was centrifuged and the Surfactin contained in the supernatant was quantitated by HPLC method under the following conditions.

| | |
|---|---|
| Amount of samples: | 20 μl |
| Column: | ODS-2, 4.6 mm × 250 mm, manufactured by GL Science Co., Ltd. |
| Column temperature: | 40° C. |
| Eluent: | 80 v/v % acetonitrile, 3.8 mM trifluoroacetic acid |
| Flow rate: | 1.5 ml/min |
| Detector: | UV detector |
| Wavelength: | 205 nm |

The quantitation was performed based on a calibration curve configured using a standard sample of Surfactin (produced by Sigma-Aldrich Co.). The amount of Surfactin based on respective nitrogen sources is shown below.

| | |
|---|---|
| Soybean flour | 5 g/L |
| Potassium nitrate | 0.6 g/L |
| Ammonium nitrate | 0.6 g/L |
| Ammonium sulfate | 0.6 g/L |
| Urea | 0.6 g/L |
| Sodium glutamate | 0.9 g/L |
| Peptone | 0.6 g/L |

EXAMPLE 4

Effect of Soybean Flour Concentration on Production of Surfactin in Test Tube Culturing

*Bacillus subtilis* SD901 (FERM BP-7666) was streaked on an L plate culture medium having added thereto 10 ppm of tetracycline and grown at 35° C. overnight. Thereafter, 1 ml of each culture medium having the following composition B, C or D was dispersed into a test tube and in respective culture mediums, one loop of cells picked up from the L plate culture medium were inoculated and cultured at 35° C. for 48 hours.

| Composition B (w/w %) | |
|---|---|
| 2% | soybean flour |
| 0.5% | $K_2HPO_4$ |
| 0.05% | $MgSO_4 \cdot 7H_2O$ |
| 0.018% | $CaCl_2 \cdot 2H_2O$ |
| 25 ppm | $FeSO_4 \cdot 7H_2O$ |
| 22 ppm | $MnCl_2 \cdot 4H_2O$ |
| 3.4% | maltose |

| Composition C (w/w %) | |
|---|---|
| 4% | soybean flour |
| 0.5% | $K_2HPO_4$ |
| 0.05% | $MgSO_4 \cdot 7H_2O$ |
| 0.018% | $CaCl_2 \cdot 2H_2O$ |
| 25 ppm | $FeSO_4 \cdot 7H_2O$ |
| 22 ppm | $MnCl_2 \cdot 4H_2O$ |
| 6.7% | maltose |

| Composition D (w/w %) | |
|---|---|
| 8% | soybean flour |
| 0.5% | $K_2HPO_4$ |
| 0.05% | $MgSO_4 \cdot 7H_2O$ |
| 0.018% | $CaCl_2 \cdot 2H_2O$ |
| 25 ppm | $FeSO_4 \cdot 7H_2O$ |
| 22 ppm | $MnCl_2 \cdot 4H_2O$ |
| 6.7% | maltose |

The culture broth was centrifuged and the Surfactin contained in the supernatant was quantitated by HPLC method. The amount of Surfactin based on each culture medium is shown below.

| | |
|---|---|
| Composition B: | 8 g/L |
| Composition C: | 16 g/L |
| Composition D: | 23 g/L |

EXAMPLE 5

Production of Surfactin in a Fermenter

*Bacillus subtilis* SD901 (FERM BP-7666) was streaked on an L plate culture medium having added thereto 10 ppm of tetracycline and grown at 35° C. overnight. From this culture broth, 100 ml of an L culture medium having added thereto 10 ppm of tetracycline was prepared in a flask with baffle and in this culture medium, one loop of cells were inoculated and cultured at 35° C. and 150 rpm for 12 hours. In a 5 L-volume fermenter, 2 L of a culture medium having the following composition E was prepared, the culture broth in the L medium was added thereto and the cells were cultured at 35° C. for 90 hours while adjusting the pH to 6.5 to 7.5 by adding 20% NaOH aqueous solution.

| Composition E (w/w %) | |
|---|---|
| 10% | soybean flour |
| 0.5% | $K_2HPO_4$ |
| 0.05% | $MgSO_4 \cdot 7H_2O$ |
| 0.018% | $CaCl_2 \cdot 2H_2O$ |
| 25 ppm | $FeSO_4 \cdot 7H_2O$ |
| 22 ppm | $MnCl_2 \cdot 4H_2O$ |
| 0.1% | yeast extract |
| 17% | maltose |
| 0.1% | L-tryptophan |
| 0.1% | L-arginine |

The culture broth was sampled in time course and the Surfactin contained in the supernatant after the centrifugation was quantitated by HPLC method. The amount of Surfactin with each culturing time is shown below.

| | |
|---|---|
| 20 hours: | 8 g/L |
| 32 hours: | 18 g/L |
| 52 hours: | 36 g/L |
| 64 hours: | 44 g/L |
| 70 hours: | 48 g/L |
| 80 hours: | 50 g/L |
| 90 hours: | 50 g/L |

INDUSTRIAL APPLICABILITY

According to the present invention, Surfactin, which is useful in the field over a wide range, such as medical preparations, agricultural chemicals, food, cosmetics, chemical products, resources/energy and environment, can be produced using an inexpensive starting material for the culture medium in a by far higher concentration as compared with conventional processes.

What is claimed is:

1. A process for producing Surfactin, comprising:
culturing a *Bacillus subtilis* strain harboring an exogenous lpa-14 gene, in a liquid culture medium, wherein said strain was subjected to chemical or physical mutagenesis and is capable of producing Surfactin in liquid culture medium in a concentration of from 8 to 50 g/L; and
accumulating Surfactin in the liquid culture medium.

2. The process for producing Surfactin as claimed in claim 1, wherein the liquid culture medium contains a bean flour or bean extract selected from the group consisting of soybean, adzuki bean, pea, broad bean, chick pea, lentil and string bean.

3. The process for producing Surfactin as claimed in claim 2, wherein said bean is soybean.

4. The process for producing Surfactin as claimed in claim 1, wherein said liquid culture medium contains a yeast extract.

5. The process for producing Surfactin as claimed in claim 1, comprising the steps of:
culturing said strain in a fermentation vessel at a pH of from 6 to 9 and a temperature of from 25 to 42° C. for 20 to 90 hours under aerobic conditions in a liquid culture medium further containing a catabolizable carbon source, a catabolizable nitrogen source and an inorganic salt,
accumulating Surfactin in the liquid culture medium without removing foam generated in the fermentation vessel, and
separating and purifying Surfactin from the obtained liquid culture medium.

6. The process for producing Surfactin as claimed in claim 1, wherein Surfactin is accumulated in the liquid culture medium in a concentration of from 8 to 50 g/L.

7. The process for producing Surfactin as claimed in claim 1, wherein the mutant obtained by said mutagenesis is *Bacillus subtilis* SD901 (FERM BP-7666).

8. The process for producing Surfactin as claimed in claim 2, wherein the concentration of bean flour or bean extract in the liquid culture medium is from 0.5 to 20 w/w %.

9. The process for producing Surfactin as claimed in claim 5, wherein the catabolizable carbon source is one or more members selected from the group consisting of glucose, maltose, sucrose, hydrolyzed starch, molasses, potato extract, malt, peat, vegetable oil, corn steep liquor, fructose, syrup, sugar, liquid sugar, invert sugar, alcohol, organic acid, organic acid salts and alkane.

10. The process for producing Surfactin as claimed in claim 9, wherein the catabolizable carbon source is glucose or maltose.

11. The process for producing Surfactin as claimed in claim 5, wherein the catabolizable nitrogen source is an ammonium salt or an inorganic or organic nitrogen.

12. The process for producing Surfactin as claimed in claim 11, wherein the ammonium salt is ammonium nitrate, ammonium sulfate, ammonium chloride, ammonium acetate, ammonium carbonate or ammonium bicarbonate.

13. The process for producing Surfactin as claimed in claim 11, wherein the inorganic or organic nitrogen is one or more members selected from the group consisting of ammonia, sodium nitrate, potassium nitrate, sodium glutamate, urea, peptone, meat extract, corn steep liquor, casein hydrolysate, feather meal and yeast extract.

14. The process for producing Surfactin as claimed in claim 5, wherein the cation contained in the inorganic salt is potassium ion, sodium ion, magnesium ion, iron ion, manganese ion, calcium ion, zinc ion, cobalt ion, nickel ion, copper ion or molybdenum ion and the anion is phosphate ion, sulfate ion, chloride ion or nitrate ion.

15. The process for producing Surfactin as claimed in claim 1, wherein an amino acid and/or a vitamin is contained in the liquid culture medium.

16. The process of producing Surfactin as claimed in claim 15, wherein the amino acid is one or more members selected from the group consisting of L-glycine, L-alanine, L-valine, L-leucine, L-isoleucine, L-serine, L-threonine, L-phenylalanine, L-tyrosine, L-cysteine, cystine, L-methionine, L-tryptophan, L-histidine, L-proline, L-asparaginic acid, L-asparagine, L-glutamic acid, L-glutamine, L-arginine, L-lysine, D-valine and D-isoleucine.

17. The process for producing Surfactin as claimed in claim 15, wherein the vitamin is one or more members selected from the group consisting of biotin, thiamin, riboflavin, pyridoxine, nicotinic acid, nicotinic acid amide, pantothenic acid, pyridoxal, pyridoxine, myo-inositol, choline, folic acid, cobalamin and cyanocobalamin.

18. The process for producing Surfactin as claimed in claim 5, wherein the pH is from 6.9 to 7.5.

19. The process for producing Surfactin as claimed in claim 5, wherein the temperature is from 30 to 37° C.

20. An isolated *Bacillus subtilis* strain harboring an exogenous lpa-14 gene, wherein said strain was subjected to chemical or physical mutagenesis and is capable of producing a crude Surfactin in a concentration of from 8 to 50 g/L on culturing for 20 to 90 hours.

21. The isolated *Bacillus subtilis* strain as claimed in claim 20, which is capable of producing Surfactin in a concentration of from 8 to 50 g/L on culturing for 20 to 90 hours in a liquid culture medium containing bean flour or bean extract.

22. The isolated *Bacillus subtilis* strain as claimed in claim 21, wherein said bean is soybean.

23. The isolated microorganism of the genus *Bacillus* as claimed in claim 20, wherein the mutant obtained by mutagenesis is *Bacillus subtilis* SD901 (FERM BP-7666).

* * * * *